United States Patent [19]

Pasqualini et al.

[11] Patent Number: 5,300,278
[45] Date of Patent: Apr. 5, 1994

[54] PROCESS FOR THE PREPARATION OF $^{99m}$TC, $^{186}$RE OR $^{188}$RE NITRIDE COMPLEXES USABLE AS RADIOPHARMACEUTICAL PRODUCTS

[75] Inventors: Roberto Pasqualini, Clanart, France; Luciano Magon, Padova, Italy; André Bardy, Morangis, France; Adriano Duatti, Del Fosso, Italy; Andrea Marchi, Ferrara, Italy

[73] Assignee: Cis Bio International, Saclay, France

[21] Appl. No.: 571,570

[22] PCT Filed: Mar. 8, 1989

[86] PCT No.: PCT/FR89/00094
§ 371 Date: Sep. 7, 1990
§ 102(e) Date: Sep. 7, 1990

[87] PCT Pub. No.: WO89/08657
PCT Pub. Date: Sep. 21, 1989

[30] Foreign Application Priority Data

Mar. 9, 1988 [FR] France ............... 88 03044
Nov. 25, 1988 [FR] France ............... 88 15414

[51] Int. Cl.$^5$ .................. A61K 49/02; A61K 43/00
[52] U.S. Cl. .......................... 534/14; 534/10
[58] Field of Search ............... 424/1.1; 534/10, 14

[56] References Cited

U.S. PATENT DOCUMENTS

| | | | |
|---|---|---|---|
| 4,374,821 | 2/1983 | Glavan et al. | 424/4 |
| 4,419,339 | 12/1983 | Neirinckx | 424/1.1 |
| 4,897,255 | 1/1990 | Fritzberg et al. | 424/1.1 |
| 4,917,879 | 4/1990 | Deutsch et al. | 424/1.1 |
| 5,002,754 | 3/1991 | Deutsch | 424/1.1 |

FOREIGN PATENT DOCUMENTS

A03063 7/1985 PCT Int'l Appl. ......... A61K 49/02
8503063 7/1985 World Int. Prop. O.

OTHER PUBLICATIONS

Chemical Abstracts, vol. 95, No. 2, Jul. 13, 1981, (Columbus, Ohio, US), L. Kaden, et al.: "Nitrido complexes of technetium(V)", p. 716.

Chemical Abstracts, vol. 102, No. 24, Jun. 17, 1985 (Columbus, Ohio, US), U. Abram et al.: "Lipophilic technetium complexes. III. Chelate complexes of technetium-nitrido core", p. 694.

"Lipophilic Technetium Complexes", Abram et al., Inorganica Chimica Acta, 109 (1985) L9-L11.

"Lipophilic Technetiun Complexes", Abram et al., Journal of Radioanalytical & Nucl. Chem., Articles, vol. 102, No. 2, (1986), 309-320.

L. Kaden et al. "Nitrido Complexes of Technitium(V), Isotopenpraxis", 1981, 17(4), 174-5, CA: 95:17322r.

Primary Examiner—Robert L. Stoll
Assistant Examiner—John M. Covert
Attorney, Agent, or Firm—Oblon, Spivak, McClelland, Maier & Neustadt

[57] ABSTRACT

The invention relates to the preparation of complexes of 99m-technetium, 186-rhenium or 188-rhenium usable as radiopharmaceutical products.

For this preparation, an oxidized compound of $^{99m}$Tc, $^{186}$Re or $^{188}$Re, e.g. an alkali metal or ammonium perrhenate or pertechnetate, is reacted with a first ligand chosen from the group of substituted or unsubstituted, aliphatic and aromatic phosphenes and polyphosphenes and a second nitrogenous ligand constituted by an ammonium nitride or a pharmaceutically acceptable metal or by a nitrogenous compound having a $>$N—N$<$ unit, such as hydrazine, a hydrazine derivative, dithiocarbazic acid and dithiocarbazic acid derivatives.

The product obtained can be used as it is as a radiopharmaceutical product or can serve as an intermediate for the preparation of other radiopharmaceutical products by exchange reaction with a third ligand, a monoclonal antibody or an antibody fragment.

22 Claims, No Drawings

PROCESS FOR THE PREPARATION OF $^{99m}$TC, $^{186}$RE OR $^{188}$RE NITRIDE COMPLEXES USABLE AS RADIOPHARMACEUTICAL PRODUCTS

DESCRIPTION

The present invention relates to a process for the preparation of complexes of a transition metal chosen from among $^{99m}$Tc, $^{186}$Re and $^{188}$Re usable as radiopharmaceutical products or for the synthesis of novel radiopharmaceutical products.

More specifically, it relates to the preparation of nitride complexes of a transition metal M chosen from among 99mTc, $^{186}$Re and $^{188}$Re having a portion M≡N in which M represents 99mTc, $^{186}$Re or $^{188}$Re.

These radioactive transition metal complexes are usable as radiopharmaceutical products in diagnosis or therapy.

Technetium 99-m complexes are more particularly used for diagnosis, whereas rhenium 186 or 188 complexes are preferably used in therapy.

The radiopharmaceutical products using the radionuclide $^{99m}$TC are compounds which are frequently used in nuclear medicine for diagnosis purposes due to the physical and chemical characteristics of said radionuclide.

Thus, the latter only gives a gamma emission, has an optimum gamma energy for the external detection (140 Kev) and has a short physical half-life (6.02 h), which only gives a low irradiation dose to the patient. In addition, the radionuclide is not expensive and is commercially available. Finally, the richness of the chemistry of technetium makes it possible to obtain a large variety of radiopharmaceutical products.

Thus, as indicated by E. DEUTSCH et al in Progr. Inorg. Chem. (Australia), vol. 30, pp. 76-106, 1983, technetium can form very varied complexes with numerous ligands in oxidation states ranging from VII to -I and coordination numbers from 4 to 9.

Among the numerous complexes of table I of pp. 79-83 of said document, are complexes of 99-Tc in oxidation state V in accordance with the formulas:

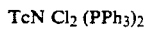

TcN Cl$_2$ (PPh$_3$)$_2$

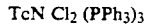

TcN Cl$_2$ (PPh$_3$)$_3$

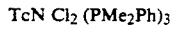

TcN Cl$_2$ (PMe$_2$Ph)$_3$

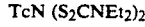

TcN (S$_2$CNEt$_2$)$_2$

These complexes were prepared by Kaden et al according to the process described in Isotopenpraxis, 1981, 17(4), pp. 174/5, with a view to use as a catalyst in the complex reduction reaction of elementary nitrogen into ammonia discovered by Volpin and Shur. This process consists of reacting $^{99}$Tc pertechnetate with hydrazine hydrochloride and triphenyl phosphine.

For this preparation, use is made of 800 mg of NH$_4$$^9$TcO$_4$-and a molar ratio of TcO$_4$—/NH$_2$NH$_2$, 2HCl of 0.46, i.e. a Tc quantity well above that which can be used for the preparation of radiopharmaceutical products or where the quantities involved represent approximately 10 mCi of $^{99m}$Tc, i.e. 8.10$^{-6}$ mg of 99mTc.

Thus, the source of $^{99m}$Tc is the $^{99}$Mo—$^{99m}$Tc generator, which generally supplies an aqueous 0.154M NaCl solution either in the pure state or containing stabilizing agents, in which the pertechnetate ion ($^{99m}$TcO$_4$$^-$+$^{99m}$TcO$_4$$^-$) is present in total concentrations between 10$^{-7}$ and 10$^{-9}$ mole/l.

In addition, the preparation process described by Kaden et al, which corresponds to a macroscopic synthesis, cannot be extrapolated to the synthesis of nitride complexes of $^{99m}$Tc on a microscopic scale, where the molar ratios between $^{99m}$Tc and the reagents are necessarily very low. Moreover, the operating procedure described by Kaden et al, which requires a separation by distillation, is not suitable for the preparation of radiopharmaceutical products and is not practical in a hospital environment, i.e. where the radiopharmaceutical products have to be prepared at the time of their use.

In addition, a process for the preparation of radiopharmaceutical products based on technetium 99m complexes and having a portion (Tc≡N)$^{2+}$ is known, which uses a completely different procedure. Thus, according to this process, which is described by J. Baldas et al in J. Chem. Soc. Dalton Trans. 1981, pp. 1798-1801, Int. J. Appl. Radiat. Ost. 36 1985, pp. 133-139 and in International Patent Application W085/03063, preparation firstly takes place of a compound of formula R+[$^{99m}$Tc≡NX$_4$], in which R+ is a cation such as sodium or ammonium and X represents a halogen atom such as Cl or Br and the compound is then reacted with an appropriate ligand to obtain the $^{99m}$Tc complex usable as a radiopharmaceutical product.

The complex R+[$^{99m}$Tc≡NX$_4$]$^-$ is of interest because it is very hydrolysis-stable and can be used without modification to the Tc≡N part for substitution reactions with other ligands, which makes it possible to obtain a wide range of technetium complexes.

The presently known process for the preparation of the intermediate compound R+[$^{99m}$TCNX$_4$]$^-$ consists of reacting a pertechnetate, such as sodium pertechnetate with sodium nitride and a halogenated hydracid, such as hydrochloric acid. In order to carry out this reaction dry evaporation takes place of a sodium pertechnetate solution (Tc-99m) using a rotary evaporator and then sodium nitride and concentrated hydrochloric acid are added to the dry residue. Refluxing takes place for approximately 5 minutes to complete the reduction and destroy the nitride excess and dry evaporation then again takes place using a rotary evaporator. This gives a residue containing the compound R+($^{99m}$Tc≡NCl$_4$)$^-$.

This process is difficult to apply to the production of medical kits, because it takes a long time and involves at least three stages in which a rotary evaporator is used twice, which is not easy to carry out in a nuclear medicine hospital department. Moreover, this process is difficult to use for the production of medical kits, because the sterility and apyrogeneity of the solutions are difficult to control throughout the operations. Therefore the product which is finally obtained must be sterilized after labelling by Tc-99m, either by passing through a sterilizing membrane, or by heat sterilization and it must be checked for the absence of pyrogen prior to injection into man.

In the case of the preparation of complexes usable in therapy, it is important to use a preparation process leading to a high yield of desired products.

However, in the case of the product developed by Baldas or Griffith (Coord. Chem. Rev., vol. 8, 1972, pp. 369-396) for the preparation of technetium nitride complexes, high complex yields are not possible. The same applies with the processes generally used for preparing rhenium-based radiopharmaceutical products.

The present invention specifically relates to a process for the preparation of nitride complexes of a transition metal chosen from among $^{99m}$Tc, $^{186}$Re and $^{188}$Re usable as radiopharmaceutical products and obviating the disadvantages of the aforementioned process.

The inventive process for the preparation of a radiopharmaceutical product incoporating a nitride complex of a transition metal chosen from among $^{99m}$Tc, $^{186}$Re and $^{188}$Re having a portion M≡N with M representing the transition metal chosen from among $^{99m}$Tc, $^{186}$Re and $^{188}$Re, is characterized in that an oxidized compound $MO_4-$ of the transition metal M is reacted with a first ligand chosen from the group of substituted or unsubstituted, aliphatic and aromatic phosphines and polyphosphines and a second nitrogenous ligand constituted either by an ammonium nitride or a pharmaceutically acceptable metal, or by a nitrogenous compound having a >N—N< unit, in which the N's are linked to hydrogen atoms and/or to monovalent organic groups via a carbon atom or in which one of the N's is linked to the carbon atom of a divalent organic group via a double bond and the other N is linked to the hydrogen atoms and/or monovalent organic groups via a carbon atom.

According to this process it is possible to easily obtain a nitride complex of a transition metal, because it is merely necessary to mix the aforementioned reagents to form the nitride complex.

Generally, the first and second ligands are used in the form of alcoholic or hydroalcoholic solutions and by the mere addition of these solutions to the oxidized compound of the transition metal, e.g. sodium pertechnetate or sodium perrhenate, a product having the sought nitride complex is directly obtained.

Thus, in this case, it is not necessary to firstly carry out the dry evaporation stages for the reagents. It is also unnecessary to sterilize the product obtained at the end of the reaction, because it is sufficient to use a sterile solution of the oxidized compound of the transition metal. In addition, the inventive process makes it possible to obtain high yields, which was not the case with the prior art processes.

The oxidized compounds of transition metals M used in the invention are salts of the type $MO_4M'$, with M' representing an alkali metal or ammonium.

In the process of the invention the first phosphine-based ligand acts as a reducing agent for the transition metal and favours the formation of M≡N, as well as the quantitative fixing of the second nitrogenous ligand. Thus, in the absence of the first ligand, it is impossible to obtain by the reaction of the second ligand with the oxidized compound of the transition metal a complex having a portion M≡N.

Preferably, according to the invention, the reaction between the oxidized compound of the transition metal and the first and second ligands takes place in an aqueous solution.

In order to carry out the reaction, it is possible to aseptically to introduce the second nitrogenous ligand and the phosphine, preferably in aqueous solution, into a container and then add the requisite quantity of the oxidized compound of the transition metal, e.g. technetium 99m pertechnetate, after having adjusted the pH to an appropriate value by adding an acid or base. It is then possible to carry out the reaction at ambient temperature or at a higher temperature between 50° and 100° C.

The temperature and pH used are more particularly dependent on the second nitrogenous ligand. Normally working takes place at pH values below 4.

Generally, the molar ratio of the oxidized compound of the transition metal to the first nitrogenous ligand is $10^{-9}$ to $10^{-4}$.

The product obtained by this process can be used as it is as a radiopharmaceutical product for therapy or diagnosis.

It can also be used as an intermediate for the production of other nitride complexes usable as radiopharmaceutical products for diagnosis or therapy. In this case, the ligands of the technetium nitride complex previously obtained are exchanged by a third organic ligand with a nucleophilic group e.g. having a better tropism for certain organs of the human body, or by a monoclonal antibody or an antibody fragment.

This exchange reaction can be carried out simultaneously, preferably in an aqueous solution, during the formation of the nitride complex by reacting together the oxidized compound of the transition metal, the first ligand, the second nitrogenous ligand and the third organic ligand with a nucleophilic group, the monoclonal antibody or the antibody fragment.

It is also possible to carry out this reaction in two stages, namely a first stage, preferably performed in an aqueous solution, in which the oxidized compound of the transition metal is reacted with the first and second ligands and then a second stage, preferably performed in an aqueous solution, in which the product obtained at the end of the first stage is reacted with the third ligand, the monoclonal antibody or the antibody fragment.

However, it is possible to carry out this exchange reaction in an alcoholic or hydroalcoholic solution. It is also possible to carry out the first and second stages in different solutions e.g. the first stage in an aqueous solution and the second stage in an alcoholic or hydroalcoholic solution or vice versa.

The organic ligands with a nucleophilic group used for this exchange reaction can vary greatly. For example, it is possible to use amines, thiols, thioethers, oximes, phosphines and polyfunctional ligands of the polyaminopolythiol type.

When the reaction is carried out with a monoclonal antibody or an antibody fragment, it is possible to prepare in this way an antibody labelled by a transition metal. For this reaction, the monoclonal antibody or the antibody fragment used can be activated, e.g. by a pretreatment with 2-amino ethane-thiol, or a reducing agent such as dithiothreitol, in order to convert the disulphide bonds into a sulphydryl group.

It is possible to use numerous antibody types and in particular those which can be linked to the M≡N portion by sulphur atoms. Examples of such antibodies are anti-ACE antibodies (anti-carcinoembryonic antigen), anti-ovarian carcinoma antibodies (OC125), antimyosin, anti-fibrin and anticolorectal antibodies.

The antibody or labelled antibody fragment obtained is very interesting, e.g. for the detection of tumours. Thus, after reaction with the transition metal complex, the monoclonal antibody or antibody fragment is linked to the transition element such as technetium 99m, but it can react with the corresponding antigens. Thus, the specificity of the antibody is maintained and the labelled antibody is stable. It is also possible to use this labelled antibody for the detection of tumours, because it will be naturally directed towards the corresponding antigen and will reveal the tumours.

In the process of the invention, the choice of the ligands used is important, because it conditions the properties of the product obtained.

The first ligand making it possible to obtain the formation of a nitride complex is an organic ligand with an electron donor phosphorus atom chosen from among substituted or unsubstituted aliphatic and aromatic phosphines and polyphosphines.

The phosphines which can be used can be in accordance with the formula:

in which $R^1$, $R^2$ and $R^3$, which can be the same or different, represent a hydrogen atom, an alkyl radical, an aryl radical, an alkoxy radical or an alkyl or aryl radical substituted by a group chosen from among the amino, amido, cyano and sulphonate radicals.

Examples of phosphines of this type are triphenyl phosphine, diethyl phenyl phosphine, triethyl phosphine, trimethyl phosphine, tris(2-cyanoethyl)-phosphine and sulphonated triphenyl phosphine. Preference is generally given to the use of triaryl phosphines as the triphenyl phosphine, because they are less oxidizable than the trialkyl phosphines.

The polyphosphines which can be used in the invention can comply with the formulas:

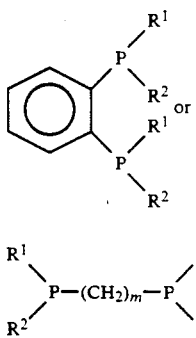

in which $R^1$, $R^2$, which can be the same or different, represent a hydrogen atom, an alkyl radical, an aryl radical, an alkoxy radical or an alkyl or aryl radical substituted by a group chosen from among amino and amido radicals and m is an integer from 1 to 4.

Examples of such polyphosphines are bis(dimethyl-1,2-phosphino)-ethane and bis(diphenyl-1,2-phosphino)-ethane.

As shown hereinbefore, the second ligand can be a nitride of a pharmaceutically acceptable metal or ammonium, or a nitrogenous compound having the unit $>N-N<$.

The nitrides of the pharmaceutically acceptable metals can in particular be alkali metal nitrides, e.g. sodium nitride.

The nitrogenous compounds having the $>N-N<$ unit can comply with the formula:

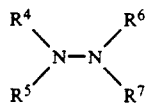

in which $R^4$, $R^5$, $R^6$ and $R^7$, which can be the same or different, represent a hydrogen atom, an alkyl radical, an aryl radical, an alkoxy radical, an alkyl radical substituted by at least one group chosen from among the hydroxy, carboxy, amino, amido and mercapto radicals, an aryl radical substituted by at least one group chosen from among the halogen atoms and alkoxy, hydroxy, amino and mercapto radical or amine radical substituted by at least one alkyl radical, a radical in accordance with the formulas:

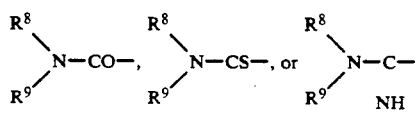

in $R^8$ and $R^9$, which can be the same or different, represent a hydrogen atom, an alkyl radical or an amino radical, a radical of formula:

in which $R^{10}$ represents a hydrogen atom, an alkyl radical or an aryl radical, a radical of formula $R^{11}$—CO— with $R^{11}$ representing an alkyl radical, an alkoxy radical, an aryl radical not substituted or substituted by at least one group chosen from among the halogen atoms and the hydroxy radicals, or a radical derived from a heterocycle which is not substituted or substituted by at least one group chosen from among the halogen atoms and the hydroxy radical, or in which $R^4$ and $R^5$ can together form a divalent radical of formula:

in which $R^{12}$ represents $-CH_2-NH_2$, an aryl radical not substituted or substituted by at least one group chosen from among the halogen atoms and the alkoxy, hydroxy, amino and mercapto radical or amino radical substituted by at least one alkyl radical, or a radical derived from a heterocycle, which is not substituted or substituted by one or more groups chosen from among halogen atoms and hydroxy, alkoxy, amino and mercapto radicals and amino radicals substituted by at least one alkyl radical and $R^{13}$ represents a hydrogen atom, an alkyl radical or an alkyl radical substituted by at least one group chosen from among hydroxy, carboxy, amino, amido and mercapto radicals and $R^6$ and $R^7$ have the meanings given hereinbefore.

These nitrogenous compounds can in particular belong to the group of hydrazine and its derivatives such as alkylhydrazines, semicarbazides, hydrazides, thiosemicarbazides, carbohydrazides, thiocarbohydrazides, acetohydrazide, hydrazine carboxylates and aminoguanidines; to the group of dithiocarbazic acid and its derivatives; and to the group of products obtained by the condensation of the aforementioned compounds with aliphatic or aromatic aldehydes or ketones.

Thus, the second nitrogenous ligand can be dithiocarbazic acid or a derivative thereof in accordance with the formula:

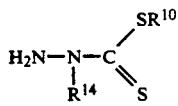

in which $R^{10}$ represents a hydrogen atom, an alkyl radical or an aryl radical and $R^{14}$ represents a hydrogen atom, an alkyl radical, an aryl radical, an alkoxy radical, an alkyl radical substituted by at least one group chosen from among hydroxy, carboxy, amino, amido and mercapto radicals, or an aryl radical substituted by at least one group chosen from among the halogen atoms and the alkoxy, hydroxy, amino and mercapto radicals and the amino radical substituted by at least one alkyl radical.

It can also be a condensation product obtained by the reaction of dithiocarbazic acid with an aliphatic aldehyde or ketone of formula $R^{15}$-CO-$R^{16}$. In this case, it complies with the formula:

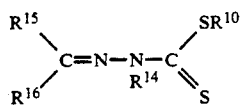

in which $R^{10}$ represents a hydrogen atom, an alkyl radical or an aryl radical, $R^{14}$ represents a hydrogen atom, an alkyl radical, an aryl radical, an alkoxy radical, an alkyl radical substituted by at least one group chosen from among the hydroxy, carboxy, amino, amido and mercapto radicals, or an aryl radical substituted by at least one group chosen from among the halogen atoms and the alkoxy, hydroxy, amino and mercapto radicals and the amino radicals substituted by at least one alkyl radical and $R^{15}$ and $R^{16}$, which can be the same or different, represent a hydrogen atom, an alkyl radical or an alkyl radical substituted by at least one group chosen from among the hydroxy, carboxy, amino, amido and mercapto radicals.

The dithiocarbazic acid derivative used as the second ligand can also be the condensation product of dithiocarbazic acid with an aromatic aldehyde or ketone. In this case, the derivative complies with the formula:

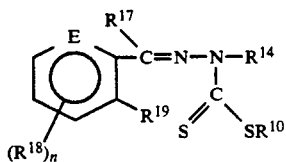

in which $R^{10}$ represents a hydrogen atom, an alkyl radical or an aryl radical, $R^{14}$ represents a hydrogen atom, an alkyl radical, an aryl radical, an alkoxy radical, an alkyl radical substituted by at least one group chosen from among the hydroxy, carboxy, amino, amido and mercapto radicals or an aryl radical substituted by at least one group chosen from among halogen atoms and alkoxy, hydroxy, amino and mercapto radicals and the amino radical substituted by at least one alkyl radical, $R^{17}$ represents a hydrogen atom, an alkyl radical, an alkyl radical substituted by at least one group chosen from among the hydroxy, carboxy, amino, amido and mercapto radicals, $R^{18}$ represents a hydrogen atom, a halogen atom, an alkoxy radical, an amino radical or an amino radical substituted by at least one alkyl group, $R^{19}$ represents a hydrogen atom, a hydroxy radical or a mercapto radical, E represents a carbon atom or a nitrogen atom and n is an integer between 1 and 4, or in which n is equal to 2 and the two $R^{18}$ are close to one another and together form an aromatic cycle.

It is also possible to use as the second ligand, the product obtained by the condensation of dithiocarbazic acid with a ketone having a 5 link heterocycle. In this case, the second ligand is in accordance with the formula:

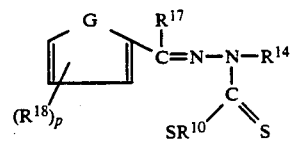

in which $R^{10}$ represents a hydrogen atom, an alkyl radical or an aryl radical, $R^{14}$ represents a hydrogen atom, an alkyl radical, an aryl radical, an alkoxy radical, an alkyl radical substituted by at least one group chosen from among the hydroxy, carboxy, amino, amido and mercapto radicals, or an aryl radical substituted by at least one group chosen from among the halogen atoms and the alkoxy, hydroxy, amino and mercapto radicals and the amino radicals substituted by at least one alkyl radical, $R^{17}$ represents a hydrogen atom, an alkyl radical, an alkyl radical substituted by at least one group chosen from among the hydroxy, carboxy, amino, amido and mercapto radicals, $R^{18}$ represents a hydrogen atom, a halogen atom, an alkoxy radical, an amino radical, or an amino radical substituted by at least one alkyl group, G is S or O and p is 1, 2 or 3.

The second ligand can also be hydrazine or a hydrazine derivative complying with the formula:

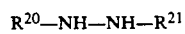

in which $R^{20}$ is a hydrogen atom or an alkyl radical and $R^{21}$ is a hydrogen atom or a radical chosen from among the radicals of formula:

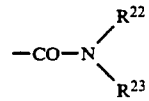

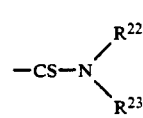

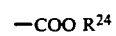

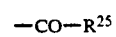

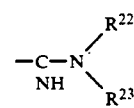

in which $R^{22}$ and $R^{23}$, which can be the same or different, represent a hydrogen atom, an alkyl radical or an amino radical, $R^{24}$ represents an alkyl radical and $R^{25}$ represents an aryl radical, which is not substituted or substituted by at least one group chosen from among the halogen atoms and the hydroxy radicals or a radical derived from a heterocycle, which is not substituted or substituted by at least one group chosen from among the halogen atoms and the hydroxy radicals.

The alkyl and alkoxy radicals used in the ligands described hereinbefore can be straight or branched radicals and generally have 1 to 3 carbon atoms.

The aryl radicals are radicals derived from a nucleus by elimination of a hydrogen atom such as phenyl and naphthyl radicals. For example, the radicals derived from heterocyclic nuclei can be furfuryl, pyridyl and thiofurfuryl radicals.

The ligands described hereinbefore are commercial products or can be prepared by conventional processes.

In the process according to the invention where the transition metal is technetium or rhenium, the nitrogenous ligands used can be monodentate, bidentate or tridentate.

Thus, it would appear that the nitride complex obtained has the square based pyramidal structure shown below in the case of Tc:

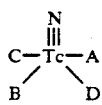

in which A represents the phosphine-based ligand and B, C and D represent the nitrogenous ligand or ligands.

In the case of a tridentate nitrogenous ligand, such as S-methyl-beta-N(2-hydroxyphenyl)methylene-dithiocarbazate of formula:

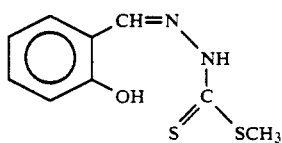

position B is occupied by one of the nitrogen atoms of the dithiocarbazate, whilst the C and D positions are occupied by the $O^-$ and $S^-$ atoms of the ionized dithiocarbazate. Therefore the complex has the following structure:

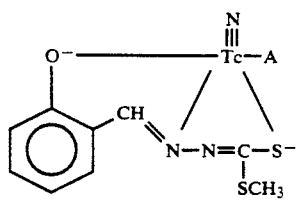

Thus, when using a tridentate nitrogenous ligand, a single complex will be obtained. However, when using monodentate nitrogenous ligands, it is possible to have different types of complexes as a function of whether the first ligand of the phosphine type occupies one or several positions A, B, C and D of the complex.

When the complex obtained from the first and second ligands is reacted with a third organic ligand with a nucleophilic group, it is necessary for said third organic ligand to be monodentate, bidentate or tetradentate in the case where the transition metal is Tc. Thus, in this case, it is possible to obtain the replacement of the first and second ligands by the third tetradentate ligand. In the case of monodentate or bidentate ligands, several complexes can be prepared, but it is found that there is generally a rearrangement of the complexes obtained in favour of the technetium complex having in particular the thrid ligand.

In the invention, the choice of the ligands used is very important, because it in particular conditions the properties of the radiopharmaceutical product obtained. Thus, by choosing a second nitrogenous ligand with a particular affinity for certain organs with Tc-99m, appropriate for scintigraphic examinations, it is possible to prepare a radiopharmaceutical composition directly usable for diagnosis. In this case, it is obviously also necessary for the first and second ligands not to be toxic and to be administrable to man.

Thus, the invention also relates to a kit for the preparation of a radiopharmaceutical product incorporating a nitride complex of $^{99m}$Tc, $^{186}$Re or $^{188}$Re comprising a first bottle containing the first ligand of the phosphine type and a second bottle containing the second nitrogenous ligand.

Thus, it is possible to directly prepare from said kit the desired radiopharmaceutical product in a nuclear medicine hospital department, by mixing the content of the two bottles and by adding thereto e.g. a solution of ammonium or alkali metal pertechnetate. The first and second ligands can be respectively present in the first and second bottles in liquid or lyophilized form.

In certain cases, it is also possible to mix in the same bottle the first and second ligands and add at the last moment the solution of the oxidized transition metal compound, e.g. pertechnetate or perrhenate, in order to prepare the radiopharmaceutical product.

As has been shown hereinbefore, it is also possible to use the transition metal complex obtained from the first and second ligands as an intermediate for the preparation of another transition metal nitride complex by exchange reaction with a third ligand, a monoclonal antibody or an antibody fragment.

The product obtained at the end of this reaction can also be used as it is as a radiopharmaceutical product for diagnosis or therapy. In this case, the kit permitting the preparation of the radiopharmaceutical product can comprise a third bottle containing the third organic ligand with a nucleophilic group, the monoclonal antibody or the antibody fragment.

Other features and advantages of the invention can be gathered from the following non-limitative, illustrative examples.

EXAMPLE 1

Into a penicillin type bottle are introduced 0.4 ml of a solution containing $2 \cdot 10^{-2}$ mole/l (2.5 mg/ml) of S-methyl dithiocarbazate (second ligand) in ethyl alcohol and then 0.2 ml of a $2 \cdot 10^{-2}$ mole/l (5 mg/ml) triphenyl phosphine solution (first ligand) in ethyl alcohol, as well as 0.1 ml of 1N hydrochloric acid. This is followed by the addition of 0.5 to 1 ml of sodium pertechnetate solution (Tc-99m) ($10^{-9}$ to $10^{-11}$ mole of Tc) and the reaction is performed at 80° C. for 30 minutes.

Thin layer chromatographic analysis of the product obtained shows that it is a technetium nitride complex with Tc≡N.

EXAMPLES 2 TO 13

The same operating procedure as in example 1 is followed in order to prepare from the ligands given in table 1, technetium nitride complexes by introducing into the bottle $5 \cdot 10^{-3}$ to $1 \cdot 10^{-2}$ mmole of the second ligand, $4 \cdot 10^{-3}$ mmole of the first ligand and 0.1 ml of 1N HCl, followed by the addition of 0.5 to 1 ml of sodium pertechnetate solution. Chromatographic analysis of the products obtained revealed that they are nitride complexes with the portion Tc≡N.

EXAMPLE 14

Into a penicillin type bottle are introduced 0.4 ml of an alcoholic solution of the second ligand constituted by a 2.5 mg/ml ($1.1 \cdot 10^{-2}$ mole/l) solution of S-methyl-beta-N(2-hydroxyphenyl) methylene dithiocarbazate in ethyl alcohol, 0.2 ml of a 5 mg/l ($2 \cdot 10^{-2}$ mole/l) triphenyl phosphine solution (first ligand) in ethyl alcohol and 0.1 ml of a 1N hydrochloric acid solution.

This is followed by the addition of 0.5 to 1 ml of a sterile sodium pertechnetate solution (technetium-99m) corresponding to a radioactivity between 18 MBq to 3.7 GBq (0.5 to 100 mCi) and the bottle is heated to 80° C. for 30 minutes.

Thin layer chromatographic analysis in the inverse Whatman KC 18 phase using as the solvent a mixture of methanol, acetonitrile, tetrahydrofuran and 0.5M ammonium acetate (proportions 3:3:2:2) reveals the appearance of a pure product with a Rf of 0.35 and confirms the presence of Tc≡N.

EXAMPLES 15 TO 22

The operating procedure of example 14 is repeated with the first and second ligands of table 2 introducing into the bottle $1 \cdot 10^{-2}$ to $3 \cdot 10^{-3}$ mmole of the second ligand. $4 \cdot 10^{-3}$ mmole of the first ligand and 0.1 ml of 1N HCl and finally adding 0.5 to 1 ml of sodium pertechnetate solution Tc-99m. At the end of the operation, the product obtained undergoes thin layer chromatography showing that the complex has the portion Tc≡N and that the phosphine forms an integral part of the complex obtained.

EXAMPLE 23

The operating procedure of example 1 is followed, but using as the second ligand 4-methyl-3-thiosemicarbazide of formula:

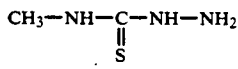

By chromatographic analysis it is established that the complex obtained is indeed a technetium nitride complex and comprises triphenyl phosphine.

EXAMPLE 24

This example adopts the same operating procedure as in example 14, but using as the second ligand the aminoacetone semicarbazone of formula:

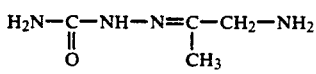

Thin layer chromatography reveals that the complex obtained is indeed a technetium nitride complex.

EXAMPLE 25

Into a penicillin type bottle are introduced 1 ml of a $5 \cdot 10^{-3}$ mole/l solution of alpha-N-methyl-S-methyl-beta-N-(2-hydroxyphenyl)-methylene dithiocarbazate in ethyl alcohol, 0.2 ml of a $6 \cdot 10^{-3}$ mole/l solution of bis(dimethyl-1,2-phosphino)-ethane of formula:

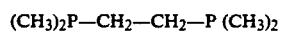

and 0.1 ml of 1N hydrochloric acid. This is followed by the addition of 0.5 ml of a sterile sodium pertechnetate solution (Tc-99m) and the bottle is heated at 80° C. for 30 minutes. This gives a technetium nitride complex having the first diphosphine-based ligand.

EXAMPLE 26

The operating procedure of example 25 is adopted, but use is made of a $5 \cdot 10^{-3}$ mole/l solution of bis(diphenyl-1,2-phosphine)-ethane and a $5 \cdot 10^{-3}$ mole/l solution of alpha-N-methyl-S-methyl-beta-N(2-hydroxyphenyl)-methylene dithiocarbazate. Once again a technetium nitride complex is obtained having the diphosphine ligand.

EXAMPLE 27

In this example, a rhenium 186 complex is prepared by introducing into a penicillin type bottle 7 mmole of triphenyl phosphine and 2 mmole of alpha-N-methyl-S-methyl-beta-N-(2-hydroxyphenyl)-methylene dithiocarbazate in alcoholic solution and 5 mmole of 1N hydrochloric acid. This is followed by the addition of 1 mmole of sodium perrhenate and the reaction is carried out at 40° C. for 30 minutes. This gives a rhenium nitride complex with a yield higher than 90%.

In the following examples, use is made of the technetium nitride complexes obtained in the preceding examples for forming other technetium complexes usable as diagnosis products.

EXAMPLE 28

This example uses the product obtained in example 14 for preparing another technetium complex with a third ligand constituted by 1,1'-(1,2-ethane diyl-diimino)-bis (2-methyl-2-propane thiol) of formula:

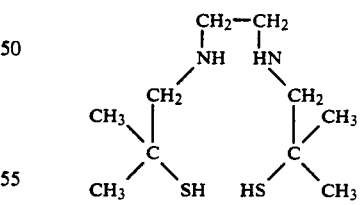

To the content of the bottle obtained in example 14 is added 0.2 ml of a $4 \cdot 10^{-2}$ mole/l 1,1'-(1,2-ethane diyl-diimino)-bis(2-methyl-2-propane thiol) solution in ethanol. The pH is brought to 9.5 by adding 0.5 ml of a 0.5M dicarbonate/carbonate buffer solution and the bottle is heated to 80° C. for 30 minutes.

The product obtained is subject to thin layer chromatography using silica gel and a solvent formed from ethanol-chloroform-benzene (2:2:1). The locations of the chromatographic spots correspond to a technetium nitride complex with the portion Tc≡N.

COMPARATIVE EXAMPLE 1

In this example reaction takes place of a 1,1'-(1,2-ethane diyl-diimino)-bis-(2-methyl-2-propane thiol) solution with sodium pertechnetate (Tc-99m) in the presence of stannous chloride. This gives an oxotechnetium diaminodithiolate analyzed by thin layer chromatography under the same conditions as the product obtained in example 27. The location of the chromatographic spots for this Tc complex containing $(TcO)^{3+}$ differs from that obtained in example 26 with the nitride complex.

EXAMPLES 29 TO 36

The same operating procedure as in example 28 is adopted for the preparation of other technetium nitride complexes from those products obtained in examples 1, 2 and 16 to 21 using as the third ligand 1,1'-(1,2-ethane diyl-diimino)-bis-(2-methyl-2-propane thiol). In all cases a technetium nitride complex having said third ligand is obtained.

EXAMPLE 37

The operating procedure of example 28 is used for preparing a novel technetium complex from the product obtained in example 1, but using as the third ligand a $6 \cdot 10^{-2}$ mole/l tetraazaundecane solution of formula:

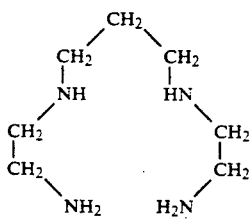

This gives a novel technetium nitride complex having tetraazaundecane as the ligand. The purity of the product is tested by thin layer chromatography using cellulose and a solvent based on ethanol-0.15M ammonium acetate (ratio 4:3).

EXAMPLES 38 TO 45

These examples follow the same operating procedure as in example 37 adding to the product obtained in examples 2, 14 and 16 to 21, 0.2 ml of a $6 \cdot 10^{-2}$ mole/l tetraazaundecane solution. In all cases a technetium nitride complex is obtained having the tetraazaundecane ligand.

EXAMPLE 46

To the content of the bottle obtained in example 16 is added 0.1 ml of a $6 \cdot 10^{-2}$ mole/l (13 mg/ml) solution of bis(1,2-dimethyl phosphine)-ethane dihydrochloride (DMPE). The pH is brought to 10 by adding 0.5 ml of a 0.5 mole/l carbonate/dicarbonate buffer solution and the reaction is carried out at 80° C. for 30 minutes.

The product obtained is analyzed by thin layer chromatography (cellulose; solvent: ethanol-0.15M ammonium acetate, 4:3). It is a technetium nitride complex with the third ligand. Thus, the chromatographic spots obtained with this complex are different from those obtained with the known technetium complexes having the formula:

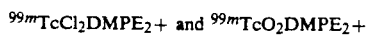

EXAMPLE 47

Preparation of a $^{99m}Tc\equiv N$ complex containing 8-mercapto quinoline a) Preparation of the intermediate Into a penicillin type bottle are introduced 0.2 ml of a solution containing $7.7 \cdot 10^{-2}$ mole/l (5 mg/ml) of sodium nitride in water and then 0.5 ml of a solution containing $5.2 \cdot 10^{-3}$ mole/l (1 mg/ml) of tris(2-cyanoethyl)-phosphine in water. This is followed by the addition of 0.5 to 5 ml of a sodium pertechnetate solution ($^{99m}Tc$) and the reaction is performed at 80° C. for 30 minutes or 100° C. for 15 minutes.

b) Preparation of the final complex

To the content of the bottle obtained in stage a), or to a fraction thereof, area added 0.3 ml of a 0.5 mole/l sodium bicarbonate-carbonate buffer solution at pH 9 and 0.4 ml of a solution containing $5 \cdot 10^{-2}$ mole/l of 8-mercapto quinoline hydrochloride (10 mg/ml) in ethanol. The reaction is performed for 15 minutes at 100° C., 30 minutes at 80° C. or 60 minutes at ambient temperature.

The radiochemical purity of the product obtained is tested by thin layer chromatography using a silica gel and a mixture of ethanol, chloroform, toluene and 0.5M ammonium acetate in the proportion 6:3:3:1. The product obtained has a Rf of 0.95, whereas $^{99m}TcO^{-4}$ has a Rf of 0.5. The radiochemical purity is equal to or better than 95%.

EXAMPLE 48

Preparation of an antibody labelled with the intermediate complex $Tc\equiv N$ d) Preparation of the intermediate.

Into a penicillin type bottle are introduced 0.4 ml of a solution containing $2 \cdot 10^{-2}$ mole/l (2.7 mg/ml) of S-methyl-N-methyl dithiocarbazate in water and then 0.5 ml of a solution containing $5.2 \cdot 10^{-3}$ mole/l of tris(2-cyanoethyl)-phosphine in water and 0.1 ml of 1N hydrochloric acid. This is followed by the addition of 0.5 to 5 ml of a sodium pertechnetate solution ($^{99m}Tc$) and the reaction is performed at 80° C. for 30 minutes or at 100° C. for 15 minutes.

b) Preparation of the labelled antibody.

To the content of the bottle obtained in stage a) adjusted to pH 7, or to a fraction thereof, is added 1 mg of whole monoclonal anti-ACE antibody (anti-carcinoembryonic antigen) pretreated by mercapto ethanol amine in order to activate the sulphydryl groups (whole activated antibody) in a 0.1M phosphate buffer solution at pH 7. The reaction takes 30 minutes at 35° C.

The radiochemical purity is tested by carrying out chromatography by filtration on gel on a type G 3000 SW (0.75×30 cm) TSK column using a 0.1M phosphate buffer at pH 7 and at a flowrate of 1 ml/minute. The radioactivity and absorbance of the sample are registered simultaneously. 95% of the radioactivity is eluted between 7 and 7.8 ml and the detectable quantity of $^{99m}TcO^{-4}$ at 12 ml is below 5%.

EXAMPLES 49 to 55

In these examples testing takes place of the properties of the complexes obtained in examples 2, 14, 17, 21, 28, 37 and 47 by determining their biodistribution in male Sprague Dawley rats weighing 200×20 g. In this case, the pentobarbital-anesthetized rats, are injected with a radiation dose of 3.7 to 10 KBq (1 to 2.7 μCi). The animals are sacrificed 5 minutes following the injection of the product. The organs are removed, washed and their radioactivity measured by means of a scintillation counter.

The results obtained are given in table 3 and are expressed as a percentage of the injected radioactivity found in the organ following sampling and counting. The values given in each box of the table represent the mean value of three experiments.

TABLE 1

2nd ligand of formula $H_2N-N\begin{matrix}R^4\\R^5\end{matrix}$

| EX | 1st ligand $4 \cdot 10^{-3}$ mmole | NAME | $(5 \cdot 10^{-3}$ to $1 \cdot 10^{-2}$ mmole) $R^4$ | $R^5$ |
|---|---|---|---|---|
| 1 | triphenyl phosphine | S-methyl dithiocarbazate | H | 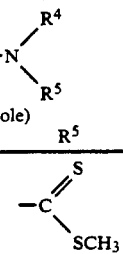 |
| 2 | triphenyl phosphine | S-methyl N-methyl dithiocarbazate | $CH_3$ | 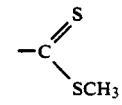 |
| 3 | triphenyl phosphine | hydrazine in dihydrochloride form $NH_2-NH_2$, 2HCl | H | H |
| 4 | triphenyl phosphine | semicarbazide in hydrochloride form $NH_2-NH-\underset{\underset{O}{\parallel}}{C}-NH_2$. HCl | H | $-\underset{\underset{O}{\parallel}}{C}-NH_2$ |
| 5 | triphenyl phosphine | thiosemicarbazide | H | $-\underset{\underset{S}{\parallel}}{C}-NH_2$ |
| 6 | triphenyl phosphine | 4-methyl-3-thio-semicarbazide | H | $-\underset{\underset{S}{\parallel}}{C}-NH-CH_3$ |
| 7 | triphenyl phosphine | carbohydrazide | H | $-\underset{\underset{O}{\parallel}}{C}-NH-NH_2$ |
| 8 | triphenyl phosphine | thiocarbohydrazide | H | $-\underset{\underset{S}{\parallel}}{C}-NH-NH_2$ |
| 9 | triphenyl phosphine | acetohydrazide | H | $-\underset{\underset{O}{\parallel}}{C}-CH_3$ |
| 10 | triphenyl phosphine | methyl hydrazine carboxylate | H | $-\underset{\underset{O}{\parallel}}{C}-OCH_3$ |
| 11 | triphenyl phosphine | furoyl-2-hydrazide | H | 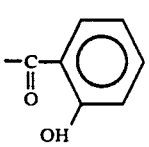 |
| 12 | triphenyl phosphine | Salicyloyl hydrazide | H | 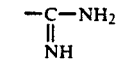 |
| 13 | triphenyl phosphine | aminoguanidine | H | $-\underset{\underset{NH}{\parallel}}{C}-NH_2$ |

TABLE 2

2nd ligand $R^{11}-CH=N-N{<}^{R^4}_{R^5}$

| EX | 1st ligand | NAME | $R^4$ | $R^5$ | $R^{11}$ |
|---|---|---|---|---|---|
| 14 | triphenyl phosphine | S-methyl β-N(2-hydroxyphenyl)methylene dithiocarbazate | H | $-\underset{S}{\overset{S}{C}}-SCH_3$ | 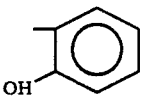 2-hydroxyphenyl |
| 15 | triphenyl phosphine | α-N-methyl S-methyl β-N(2-hydroxyphenyl) methylene dithiocarbazate | $CH_3$ | " | " |
| 16 | triphenyl phosphine | α,N-methyl-S-methyl β-N pyridylmethylene dithiocarbazate | " | " | 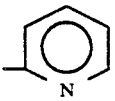 pyridyl |
| 17 | diethyl phenyl phosphine | S-methyl β, N(2-hydrophenyl)methylene dithiocarbazate | H | " | 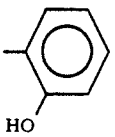 2-hydroxyphenyl |
| 18 | triphenyl phosphine | S-methyl-β, N(2,5-dihydroxy-phenyl) methylene dithiocarbazate | H | $-\underset{S}{\overset{S}{C}}-SCH_3$ | 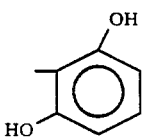 2,5-dihydroxyphenyl |
| 19 | diethyl phenyl phosphine | S-methyl-β, N(2,5-dihydroxy-phenyl) methylene dithiocarbazate | " | " | " |
| 20 | triethyl phosphine | S-methyl-β, N(2,5-dihydroxy-phenyl) methylene dithiocarbazate | " | " | " |
| 21 | trimethyl phosphine | S-methyl-β, N(2,5-dihydroxy-phenyl) methylene dithiocarbazate | " | " | " |
| 22 | triphenyl phosphine trisulphonate | α-N-methyl S-methyl β-N(2-hydroxyphenyl) methylene dithiocarbazate | $CH_3$ | " | 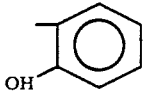 2-hydroxyphenyl |

TABLE 3

| | Ex. 49 | Ex. 50 | Ex. 51 | Ex. 52 | Ex. 53 | Ex. 54 | Ex. 55 |
|---|---|---|---|---|---|---|---|
| Whole organs | Complex of example 2 | Complex of example 14 | Complex of example 17 | Complex of example 21 | Complex of example 28 | Complex of example 37 | Complex of example 47 |
| Liver | 19.71 | 32.41 | 35.64 | 20.23 | 12.42 | 13.63 | 7.30 |
| Kidneys | 7.02 | 0.80 | 2.09 | 4.54 | 14.70 | 19.61 | 0.87 |
| Lungs | 5.54 | 2.89 | 2.07 | 2.86 | 1.11 | 0.84 | 12.64 |
| Brain | 0.22 | 0.06 | 0.15 | 0.56 | 0.08 | 0.06 | 0.19 |
| Heart | 0.82 | 0.48 | 0.90 | 0.67 | 0.35 | 0.24 | 0.23 |
| Blood | 18.03 | 32.22 | 17.58 | 15.06 | 7.56 | 10.38 | 0.84 |

We claim:

1. A process for the preparation of a radiopharmaceutical product incorporating a nitride complex of a transition metal selected from the group consisting of $^{99m}Tc$, $^{186}Re$ and $^{188}Re$, having a portion M≡N with M representing the transition metal, characterized in that about $10^9$–$10^{11}$ moles of an oxidized compound, $MO_4^-$, of the transition metal M is reacted with a first ligand selected from the group consisting of substituted or unsubstituted aliphatic and aromatic phosphines and polyphosphines, and a second nitrogenous ligand consisting of either an ammonium nitride or a pharmaceutically acceptable metal nitride, or of a nitrogenous compound having a >N—N< unit, in which the Ns are linked with the hydrogen atoms and/or monovalent organic groups via a carbon atom, or in which one of the ends is linked with the carbon atom of a divalent organic group via a double bond and the other N is linked with the hydrogen atoms and/or monovalent organic groups via a carbon atom.

2. A process according to claim 1, characterized in that the reaction is performed in an aqueous solution.

3. A process according to claim 1 wherein the radiopharmaceutical produced is sterile and apyrogenic.

4. A process as claimed in claim 1 wherein 0.5 to 100 mCi of transition metal is reacted with a first and a second ligand.

5. A process according to claim 1, wherein $10^{-9}$–$10^{-11}$ mole of $MO_4^-$ is reacted with a first and a second ligand.

6. A process as claimed in claim 5 wherein the molar ratio of $MO_4^-$ to the nitrogenous ligand is from $10^{-9}$ to $10^{-4}$.

7. A process according to claim 1, consisting of:
 1) adding solutions of the first and the second ligands to a container,
 2) adjusting the pH of the solution obtained in 1) to a value below 4, and
 3) adding $10^{-9}$–$10^{-11}$ moles of the oxidized compound of the transition metal to the solution obtained in 2) above.

8. A process according to claim 1, characterized in that the oxidized compound of the transition metal is a -99m pertechnetate of alkali metal or ammonium.

9. A process according to claim 1, characterized in that the oxidized compound of the transition metal is -186 or -188 perrhenate of alkali metal or ammonium.

10. A process according to claim 1, characterized in that the first ligand is a phosphine complying with the formula:

in which $R^1$, $R^2$ and $R^3$, which can be the same or different, represent a hydrogen atom, a $C_1$-$C_3$ alkyl radical, a phenyl radical, a naphthyl radical, a $C_1$-$C_3$ alkoxy radical or said $C_1$-$C_3$ alkyl, phenyl or naphthyl radical substituted by a group selected from the group consisting of amino, amido, cyano and sulphonate radicals.

11. A process according to claim 10, characterized in that the first ligand is a phosphine selected from the group consisting of triphenyl phosphine, diethyl phenyl phosphine, triethyl phosphine, trimethyl phosphine and tris(2-cyanoethyl)-phosphine.

12. A according to claim 1, characterized in that the first ligand is a polyphosphine complying with one of the formulas:

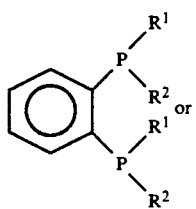

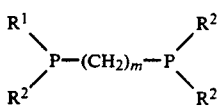

in which $R^1$, and $R^2$, which can be the same or different, represent a hydrogen atom, a $C_1$-$C_3$ alkyl radical, a phenyl radical, a naphthyl radical, a $C_1$-$C_3$ alkoxy radical or said $C_1$-$C_3$ alkyl, phenyl or naphthyl radical substituted by a group selected from the group consisting of amino and amido radicals and m is an integer between 1 and 4.

13. A process according to claim 1, characterized in that the second ligand is a nitrogenous compound complying with the formula:

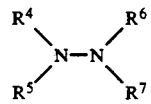

in which $R^4$, $R^5$, $R^6$ and $R^7$, which can be the same or different, represent a hydrogen atom, a $C_1$-$C_3$ alkyl radical, a phenyl radical, a naphthyl radical, a $C_1$-$C_3$ alkoxy radical, said $C_1$-$C_3$ alkyl radical substituted by at least one group selected from the group consisting of hydroxy, carboxy, amino, amido and mercapto radicals, said phenyl or naphthyl radical substituted by at least one group selected from the group consisting of halogen atoms and alkoxy, hydroxy, amino and mercapto radicals an amine radical substituted by at least one $C_1$-$C_3$ alkyl radical, a radical in accordance with the formulas:

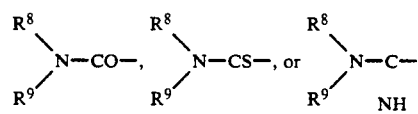

in which $R^8$ and $R^9$, which can be the same or different, represent a hydrogen atom, a $C_1$-$C_3$ alkyl radical or an amino radical, a radical of formula:

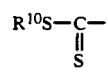

in which $R^{10}$ represents a hydrogen atom, a $C_1$-$C_3$ alkyl radical, a phenyl radical or a naphthyl radical, a radical of formula $R^{11}$—CO— with $R^{11}$ representing a $C_1$-$C_3$ alkyl radical, a $C_1$-$C_3$ alkoxy radical, a phenyl or naphthyl radical not substituted or substituted by at least one group selected from the group consisting of halogen atoms and hydroxy radicals, or a radical derived from a heterocycle and selected from the group consisting of furfuryl, pyridyl and thiofuryl radicals which are not substituted or are substituted by at least one group selected from the group consisting of halogen atoms and hydroxy radicals, or in which $R^4$ and can together form a divalent radical of formula:

in which $R^{12}$ represents —$CH_2$—$NH_2$, a phenyl or naphthyl radical not substituted or substituted by at least one group selected from the group consisting of halogen atoms and $C_1$-$C_3$ alkoxy, hydroxy, amino and mercapto radicals or an amino radical substituted by at least one $C_1$-$C_3$ alkyl radical, or a radical derived from a heterocycle and selected from the group consisting of furfuryl, pyridyl and thiofuryl radicals, which is not substituted or is substituted by one or more groups selected from the group consisting of halogen atoms and hydroxy, $C_1$-$C_3$ alkoxy, amino and mercapto radicals and amino radical radicals substituted by at least one $C_1$-$C_3$ alkyl radical and $R^{13}$ represents a hydrogen atom, a $C_1$-$C_3$ alkyl radical or a $C_1$-$C_3$ alkyl radical substituted by at least one group selected from the group consisting of hydroxy, carboxy, amino, amido and mercapto radicals and $R^6$ and $R^6$ have the meaning given hereinbefore.

14. A process according to claim 1, characterized in that the second ligand is a dithiocarbazic acid or a derivative thereof complying with the formula:

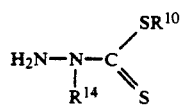

in which $R^{10}$ represents a hydrogen atom, an alkyl radical or an aryl radical and $R^{14}$ represents a hydrogen atom, an alkyl radical, an aryl radical, an alkoxy radical, an alkyl radical substituted by at least one group selected from the group consisting of hydroxy, carboxy, amino, amido and mercapto radicals, or an aryl radical substituted by at least one group selected from the group consisting of halogen atoms and alkoxy, hydroxy, amino and mercapto radicals and an amino radical substituted by at least one alkyl radical wherein said alkyl and alkoxy radicals have from 1 to 3 carbon atoms and wherein said aryl radical is selected from the group consisting of phenyl and naphthyl radicals.

15. A process according to claim 1, characterized in that the second ligand is a condensation product of dithiocarbazic acid in accordance with the formula:

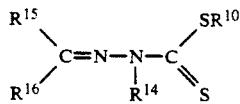

in which $R^{10}$ represents a hydrogen atom, an alkyl radical or an aryl radical and $R^{14}$ represents a hydrogen atom, an alkyl radical, an aryl radical, an alkoxy radical, an alkyl radical substituted by at least one group selected from the group consisting of hydroxy, carboxy, amino, amido and mercapto radicals, or an aryl radical substituted by at least one group selected from the group consisting of halogen atoms and alkoxy, hydroxy, amino and mercapto radicals and amino radical substituted by at least one alkyl radical and amino radicals substituted by at least one alkyl radical and $R^{15}$ and $R^{16}$, which can be the same or different, represent a hydrogen atom, an alkyl radical or an alkyl radical substituted by at least one group selected from the group consisting of hydroxy, carboxy, amino, amido and mercapto radicals wherein said alkyl and alkoxy radicals have from 1 to 3 carbon atoms and wherein said aryl radical is selected from the group consisting of phenyl and naphthyl radicals.

16. A process according to claim 1, characterized in that the second ligand is a condensation product of dithiocarbazic acid in accordance with the formula:

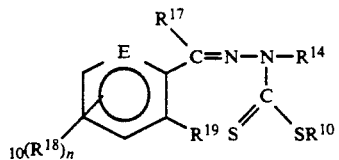

in which $R^{10}$ represents a hydrogen atom, an alkyl radical or an aryl radical, $R^{14}$ represents a hydrogen atom, an alkyl radical, an aryl radical, an alkoxy radical, an alkyl radical substituted by at least one group selected from the group consisting of hydroxy, carboxy, amino, amido and mercapto radicals, or an aryl radical substituted by at least one group selected from the group consisting of halogen atoms and alkoxy, hydroxy, amino and mercapto radical, and an amino radical substituted by at least one alkyl radical, $R^{17}$ represents a hydrogen atom, an alkyl radical, an alkyl radical substituted by at least one group selected from the group consisting of hydroxy, carboxy, amino, amido and mercapto radicals, $R^{18}$ represents a hydrogen atom, a halogen atom, an alkoxy radical, an amino radical or an amino radical substituted by at least one alkyl group, $R^{19}$ represents a hydrogen atom, a hydroxy radical or a mercapto radical, E represents a carbon atom or a nitrogen atom and n is an integer between 1 and 4, or in which n is equal to 2 and the two $R^{18}$ together form an aromatic cycle wherein said alkyl and alkoxy radicals have from 1 to 3 carbon atoms and wherein said aryl radical is selected from the group consisting of phenyl and naphthyl radicals.

17. A process according claim 1, characterized in that the second ligand is a condensation product of dithiocarbazic acid in accordance with the formula:

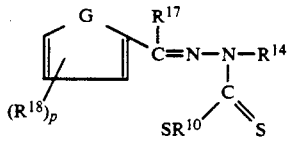

in which $R^{10}$ represents a hydrogen atom, an alkyl radical or a aryl radical, $R^{14}$ represents a hydrogen atom, an alkyl radical, an aryl radical, an alkoxy radical, an alkyl radical substituted by at least one group selected from the group consisting of hydroxy, carboxy, amino amido and mercapto radicals, or an aryl radical substituted by at least one group selected from the group consisting of halogen atoms and alkoxy, hydroxy, amino and mercapto radicals and amino radicals substituted by at least one alkyl radical, $R^{17}$ represents a hydrogen atom, an alkyl radical, an alkyl radical substituted by at least one group selected from the group consisting of hydroxy, carboxy, amino, amido and mercapto radicals, $R^{18}$ represents a hydrogen atom, a halogen atom, an alkoxy radical, an amino radical, or an amino radical substituted by at least one alkyl group, G is S or O and p is 1, 2 or 3 wherein said alkyl and alkoxy radicals have from 1 to 3 carbon atoms and wherein said aryl radical is selected from the group consisting of phenyl and naphthyl radicals.

18. A process according to claim 1, characterized in that the second ligand is hydrazine or a hydrazine derivative complying with the formula:

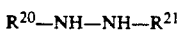

in which $R^{20}$ is a hydrogen atom or an alkyl radical and $R^{21}$ is a hydrogen atom or a radical chosen from among the radicals of formula:

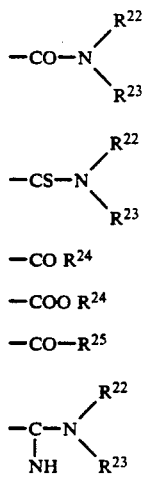

in which $R^{22}$ and $R^{23}$, which can be the same or different, represent a hydrogen atom, an alkyl radical or an amino radical, $R^{24}$ represents an alkyl radical and $R^{25}$ represents an aryl radical which is not substituted or which is substituted by at least one group selected from the group consisting of halogen atoms and hydroxy radicals or a furfuryl, pyridyl or thiofurfuryl radical which is not substituted or is substituted by at least one group selected from the group consisting of halogen atoms and hydroxy radicals wherein said alkyl and alkoxy radicals have from 1 to 3 carbon atoms and wherein said aryl radical is selected from the group consisting of phenyl and naphthyl radicals.

19. A process according to claim 1, characterized in that the second ligand is selected from the group consisting of S-methyl-beta-N(2-hydroxyphenyl) methylene dithiocarbazate, S-methyldithiocarbazate, S-methyl N-methyldithiocarbazate, alpha-N-methyl-S-methyl-beta-N-pyridylmethylene dithiocarbazate, S-methyl-beta-N-(2,5-dihydroxyphenyl) methylene dithiocarbazate, alpha-N-methyl-S-methyl-N(2-hydroxyphenyl) methylene dithiocarbazate, hydrazine, semicarbazide, thiosemicarbazide, 1-methyl-3-thiosemicarbazide, 4-methyl-3-thiosemicarbazide, aminoacetonesemicarbazone, carbohydrazide, thiocarbohydrazide, aceto-hydrazide, methylhydrazinecarboxylate, 2-furoyl hydrazide, salicyloyl hydrazide, aminoguanidine and sodium nitride.

20. A process for the preparation of a radiopharmaceutical product incorporating a nitride complex of a transition metal selected from the group consisting of $^{99m}$Tc, $^{186}$Re and $^{188}$Re, having a portion M≡N with M representing the transition metal, characterized in that an oxidized compound, $MO_4^-$, of the transition metal M is reacted with a first ligand selected from the group consisting of substituted or unsubstituted aliphatic and aromatic phosphines and polyphosphines, and a second nitrogenous ligand consisting of either an ammonium nitride or a pharmaceutically acceptable metal nitride, or of a nitrogenous compound having a >N-N< unit, in which the Ns are linked with the hydrogen atoms and/or monovalent organic groups via a carbon atom, or in which one of the ends is linked with the carbon atom of a divalent organic group via a double bond and the other N is linked with the hydrogen atoms and/or monovalent organic groups via a carbon atom, wherein the molar ratio of $MO_4^-$ to the nitrogenous ligand is from about $10^{-9}$ to about $10^{-4}$.

21. A process as claimed in claim 20 wherein the molar ratio of $MO_4^-$ to the nitrogenous ligand is from $10^{-9}$ to $10^{-4}$.

22. A process for the preparation of a radiopharmaceutical product incorporating a nitride complex of a transition metal selected from the group consisting of $^{99m}$Tc, $^{186}$Re and $^{188}$Re, having a portion M≡N with M representing the transition metal, characterized in that an oxidized compound, $MO_4^-$, of the transition metal M is reacted with a first ligand selected from the group consisting of substituted or unsubstituted aliphatic and aromatic phosphines and polyphosphines and a second nitrogenous ligand characterized in that the second nitrogenous ligand is an alkali metal nitride.

* * * * *